US009725704B2

(12) United States Patent
Kueppers et al.

(10) Patent No.: US 9,725,704 B2
(45) Date of Patent: Aug. 8, 2017

(54) EXPRESSION METHOD

(71) Applicant: BASF SE, Ludwigshafen (DE)

(72) Inventors: Tobias Kueppers, Moenchengladbach (DE); Victoria Steffen, Juelich (DE); Renee Charlott Eichstadt, Cologne (DE); Stefan Evers, Mettmann (DE); Karl-Heinz Maurer, Erkrath (DE); Johannes Bongaerts, Dormagen (DE); Hendrik Hellmuth, Duesseldorf (DE); Thomas Weber, Dormagen (DE); Timothy O'Connell, Duesseldorf (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/374,556

(22) PCT Filed: Jan. 29, 2013

(86) PCT No.: PCT/EP2013/051656
§ 371 (c)(1),
(2) Date: Jul. 25, 2014

(87) PCT Pub. No.: WO2013/113689
PCT Pub. Date: Aug. 8, 2013

(65) Prior Publication Data
US 2014/0370569 A1    Dec. 18, 2014

(30) Foreign Application Priority Data
Jan. 31, 2012  (DE) .................. 10 2012 201 297

(51) Int. Cl.
*C12N 9/26* (2006.01)
*C12N 9/50* (2006.01)
*C12N 1/20* (2006.01)
*C12N 15/74* (2006.01)
*C12P 21/06* (2006.01)
*C12P 19/34* (2006.01)
*C12N 15/75* (2006.01)
*C12P 21/02* (2006.01)
*C12N 9/00* (2006.01)
*C12N 9/54* (2006.01)

(52) U.S. Cl.
CPC .............. *C12N 9/2411* (2013.01); *C12N 9/00* (2013.01); *C12N 9/2414* (2013.01); *C12N 9/50* (2013.01); *C12N 9/54* (2013.01); *C12N 15/75* (2013.01); *C12P 21/02* (2013.01)

(58) Field of Classification Search
CPC . C12N 15/75; C12N 9/00; C12N 9/50; C12N 9/2411; C12N 9/2414; C12N 9/54; C12P 21/02
USPC .......... 435/201, 219, 252.31, 471, 477, 485, 435/69.1, 91.1
See application file for complete search history.

(56) References Cited

U.S. PATENT DOCUMENTS

| 5,646,044 A | 7/1997 | Wilson et al. | |
|---|---|---|---|
| 5,958,728 A * | 9/1999 | Sloma | C12N 15/75 435/252.31 |
| 7,494,798 B2 * | 2/2009 | Berka | C07K 14/32 435/209 |
| 8,518,669 B2 * | 8/2013 | Koyama | C12N 9/88 435/232 |
| 2011/0020938 A1 | 1/2011 | Koyama et al. | |

FOREIGN PATENT DOCUMENTS

| CN | 100372937 C | 3/2008 |
|---|---|---|
| EP | 0 501 765 A1 | 9/1992 |
| EP | 2 196 533 A1 | 6/2010 |
| JP | S63-214187 A | 9/1988 |
| WO | WO-99/43835 A2 | 9/1999 |
| WO | WO-00/53778 A1 | 9/2000 |
| WO | WO-02/088340 A2 | 11/2002 |

OTHER PUBLICATIONS

Eder et al., Mutational analysis of the phoD promoter in *Bacillus subtilis*: Implications for PhoP binding and promoter activation of Pho regulon promoters. J. Bacteriol., 1999, vol. 181(7): 2017-2025.*
Nahrstedt et al., Strain development in *Bacillus licheniformis*: Construction of biologically contained mutants deficient in sporulation and DNA repair. J. Biotechnol., 2005, vol. 119: 245-254.*
Phan et al., Development of a strong intacellular expression system for *Bacillus subtilis* by optimizing promoter elements. J. Biotechnol., 2012, vol. 157: 167-172.*
Satola et al., Binding of Spo0A stimulates spoIIG promoter activity. J. Bacteriol., 1992, vol. 174(5): 1448-1453.*
Gioia, et al., "Paradoxical DNA Repair and Peroxide Resistance Gene Conservation in *Bacillus pumilus* SAFR-032," PLoS One, Public Library of Science, US, 2007, vol. 2, No. 9, p. e928.
International Search Report in International Application No. PCT/EP2013/051656, dated Apr. 24, 2013.
Feng, et al., "Fermentation of Starch for Enhanced Alkaline Protease Production by Constructing an Alkalophilic *Bacillus Pumilus* Strain," Applied Microbiology and Biotechnology, 2001 vol. 57, No. 1-2, pp. 153-160.
Schallmey, et al., "Developments in the Use of Bacillus Species for Industrial Production," Canadian Journal of Microbiology, 2004, vol. 50, No. 1, pp. 1-17.
Office Action, Japanese patent application No. 2014-553753, dated Nov. 21, 2016.

(Continued)

Primary Examiner — Ganapathirama Raghu
(74) Attorney, Agent, or Firm — Marshall, Gerstein & Borun LLP

(57) ABSTRACT

In a microbial fermentation, the aim is to increase the product yield of protein. This is achieved by a method in which an expression construct is introduced into a microorganism of the species *Bacillus pumilus* which comprises a promoter and a nucleic acid coding for the protein, and the protein is expressed in said expression construct.

12 Claims, No Drawings

(56) References Cited

OTHER PUBLICATIONS

Palva, et al., "Nucleotide sequence of the promoter and $NH_2$-terminal signal peptide region of the α-amylase gene from *Bacillus amyloliquefaciens*", *Gene*, 15:43-51 (1981).

Tatsuro, et al., "Purification and molecular characterization of glutamyl endopeptidase from zein-utilizing *Bacillus pumilus* strain MS-1", *Food Preservation Science*, 32(1):5-11 (2006).

* cited by examiner

EXPRESSION METHOD

CROSS-REFERENCE TO RELATED APPLICATIONS

This is the U.S. national phase of International Application No. PCT/EP2013/051656, filed Jan. 23, 2013, which claims the benefit of European patent Application no. 10 2012 201 297.4, filed Jan. 31, 2012.

The invention is in the field of biotechnology, in particular microbial protein synthesis. The invention relates in particular to a method for producing proteins by means of genetically modified microorganisms and also proposes microorganisms which are used in such methods. The invention further relates to uses of such microorganisms for protein production.

Microorganisms can be used for producing products of value. Products of value are, for example, low molecular weight compounds, for example food supplements or pharmaceutically effective compounds, or proteins, for which there is in turn a large technical field of use on account of their diversity. In the first case, the metabolic properties of the microorganisms in question are utilized and/or modified for producing the products of value; in the second case, preference is given to using microorganisms which express the genes of the proteins of interest.

For large-scale industrial, biotechnological production, the microorganisms in question are cultivated in fermenters which are configured accordingly to the metabolic properties of the microorganisms. During the cultivation, the microorganisms metabolize the supplied substrate and form the desired product which, after the fermentation is complete, is usually separated off from the production organisms and purified and/or concentrated from the fermenter broth and/or the fermentation medium. During the fermentative production of proteins, complex protein-rich raw materials are typically used as substrate alongside a carbon source (typically glucose). The protein production thus corresponds to a biotransformation of substrate protein to the target protein. This requires the complete hydrolysis of the substrate protein into the individual amino acids, which are then available for the biosynthesis of the target protein.

As regards the fermentation of microorganisms, there is consequently extensive prior art which ranges from the optimization of the strains in question, for example as regards the formation rate and the nutrient utilization, via the technical design of the fermenters to the isolation of the products of value from the microorganisms in question and/or the fermentation medium.

The use of bacteria in microbial fermentations is fundamentally desirable. Bacteria are characterized by short generation times and low demands on the cultivation conditions. As a consequence, cost-effective cultivation methods and/or production methods can be established. Moreover, the person skilled in the art has a wealth of experience with bacteria in fermentation technology. Preference is given to using Gram-positive bacteria since they secrete the protein to be produced (target protein) into the medium surrounding them.

Usually, the highest possible product yields are desirable during microbial fermentation. For example, the international patent application WO 91/02792 discloses the improved fermentative production of an alkaline protease from *Bacillus lentus* in an optimized *Bacillus licheniformis* strain under the control of gene-regulatory sequences from *Bacillus licheniformis*, in particular the *Bacillus licheniformis* promoter.

Alternative production organisms to *Bacillus licheniformis* with which comparably high or even improved product yields can be attained are not satisfactorily available in the prior art. There is also a great need for microbial fermentation methods which permit a high product yield.

It is the object of the present invention to attain a high product yield, in particular of a protein, in a microbial fermentation.

The invention provides a method for producing a protein by means of a microorganism comprising the method steps
(a) introducing an expression construct into a microorganism which comprises a promoter and a nucleic acid coding for the protein;
(b) expression of the protein in the microorganism,
where the microorganism belongs to the species *Bacillus pumilus*.

A method according to the invention optionally also comprises the further method step
(c) cultivation of the microorganism.

In preferred embodiments according to the invention, a method according to the invention is consequently a fermentation method.

Surprisingly, it has been found that the use of a bacterium of the species *Bacillus pumilus* in such a method permits a high product yield and is therefore advantageous. By using *Bacillus pumilus* as production organism it is possible to attain an advantageous, in particular increased, product yield. The reference used in this regard is *Bacillus licheniformis*, a production organism established in the prior art which is used industrially in a large number of microbial fermentations.

In a preferred embodiment, the method according to the invention is consequently a method for increasing the expression of a protein in a microorganism. Increased expression of the protein is present if a larger amount of protein is obtained as a result of a method according to the invention compared to a comparable method which differs from a method according to the invention merely by virtue of the fact that bacteria of the species *Bacillus licheniformis*, preferably of the wild type, are used. Both methods that are to be compared are in this respect carried out under identical conditions that are as optimal as possible for the microorganisms and for the same time.

An expression construct is a nucleic acid sequence which causes the protein in the microorganism to be able to be expressed. It comprises the genetic information, i.e. the nucleic acid sequence (gene) which codes for the protein. The expression of a nucleic acid sequence is its translation into the gene product(s) coded by this sequence, i.e. into one or more polypeptides (protein or proteins). The terms polypeptide and protein are used synonymously in the present application. In the context of the present invention, expression consequently refers to the biosynthesis of ribonucleic acid (RNA) and proteins from the genetic information. As a rule, the expression comprises transcription, i.e. the synthesis of a messenger ribonucleic acid (mRNA) by reference to the DNA (deoxyribonucleic acid) sequence of the gene and its translation into the corresponding polypeptide chain, which can optionally also be posttranslationally modified. The expression of a protein consequently describes the biosynthesis of the same from the genetic information which is present according to the invention in the microorganism.

An expression construct further comprises at least one nucleic acid sequence, preferably DNA, with a control function for the expression of the nucleic acid sequence coding for the protein or the auxiliary protease (so-called gene-regulatory sequence). A gene-regulatory sequence here is any nucleic acid sequence whose presence in the microorganism influences, preferably increases, the transcription frequency of the nucleic acid sequence which codes for the protein. It is preferably a promoter sequence since such a sequence is essential for the expression of a nucleic acid sequence. An expression construct according to the invention can, however, also comprise further gene-regulatory sequences, for example one or more enhancer sequences. In the context of the invention, an expression construct consequently comprises at least one functional unit of gene and promoter. It can, but need not necessarily, be present as a physical entity.

The presence of at least one promoter is essential for an expression construct according to the invention. A promoter is accordingly understood as meaning a DNA sequence which allows the regulated expression of a gene. A promoter sequence is naturally a constituent of a gene and is often situated at its 5' end and thus before the RNA-coding region. Preferably, the promoter sequence in an expression construct according to the invention is situated 5' upstream of the nucleic acid sequence coding for the protein. The most important property of a promoter is the specific interaction with at least one DNA-binding protein or polypeptide which mediates the start of the transcription of the gene by means of an RNA polymerase and is referred to as a transcription factor. Several transcription factors and/or further proteins are often involved at the start of the transcription by means of an RNA polymerase. A promoter is accordingly preferably a DNA sequence with promoter activity, i.e. a DNA sequence onto which at least one transcription factor binds at least transiently in order to initiate the transcription of a gene. The strength of a promoter is measurable via the transcription frequency of the expressed gene, i.e. via the number of RNA molecules produced per time unit, in particular mRNA molecules. A promoter of an expression construct according to the invention can be an endogenous promoter of the microorganism. Such a promoter sequence is consequently naturally present in the microorganism. Alternatively, a promoter of an expression construct according to the invention can also have been introduced recombinantly into the microorganism. The same is true for all further gene-regulatory sequences which an expression construct according to the invention can have. The promoter in an expression construct, as is used in a method according to the invention, brings about the expression of the nucleic acid sequence coding for the protein (target protein) in the expression construct.

In a preferred embodiment, a method according to the invention is one wherein the promoter comprises a nucleic acid sequence which is selected from
(a) nucleic acid sequence which is at least 80% and increasingly preferably at least 81%, 82%, 83%, 84%, 85%, 86%, 87%, 88%, 89%, 90%, 91%, 92%, 93%, 94%, 95%, 96%, 97%, 98%, 99%, 99.2%, 99.3%, 99.4%, 99.5% and very particularly preferably 100%, identical to the nucleic acid sequence given in SEQ ID No. 1;
(b) nucleic acid sequence which is at least 80% and increasingly preferably at least 81%, 82%, 83%, 84%, 85%, 86%, 87%, 88%, 89%, 90%, 91%, 92%, 93%, 94%, 95%, 96%, 97%, 98%, 99%, 99.2%, 99.3%, 99.4%, 99.5% and very particularly preferably 100%, identical to the nucleic acid sequence given in SEQ ID No. 2;
(c) nucleic acid sequence which is at least 80% and increasingly preferably at least 81%, 82%, 83%, 84%, 85%, 86%, 87%, 88%, 89%, 90%, 91%, 92%, 93%, 94%, 95%, 96%, 97%, 98%, 99%, 99.2%, 99.3%, 99.4%, 99.5% and very particularly preferably 100%, identical to the nucleic acid sequence given in SEQ ID No. 3;
(d) nucleic acid sequence which is at least 80% and increasingly preferably at least 81%, 82%, 83%, 84%, 85%, 86%, 87%, 88%, 89%, 90%, 91%, 92%, 93%, 94%, 95%, 96%, 97%, 98%, 99%, 99.2%, 99.3%, 99.4%, 99.5% and very particularly preferably 100%, identical to the nucleic acid sequence given in SEQ ID No. 4.

In an alternative embodiment, the promoter has a nucleic acid sequence as described above.

It has been found that particularly high product yields of protein can be attained in a method according to the invention with such promoter sequences.

Preferably, the promoter is one which comprises a nucleic acid sequence which is at least 80% and increasingly preferably at least 81.0%, 82.0%, 83.0%, 84.0%, 85.0%, 86.0%, 87.0%, 88.0%, 89.0%, 90.0%, 91.0%, 92.0%, 93.0%, 94.0%, 95.0%, 96.0%, 97.0%, 98.0%, 99.0%, 99.2%, 99.3%, 99.4%, 99.5% and very particularly preferably 100%, identical to the nucleic acid sequence given in SEQ ID No. 1, and the promoter brings about a transcription frequency of the gene expressed by it which corresponds at least to that of a promoter according to SEQ ID No. 1. Alternatively, the promoter is one which comprises a nucleic acid sequence which is at least 80% and increasingly preferably at least 81.0%, 82.0%, 83.0%, 84.0%, 85.0%, 86.0%, 87.0%, 88.0%, 89.0%, 90.0%, 91.0%, 92.0%, 93.0%, 94.0%, 95.0%, 96.0%, 97.0%, 98.0%, 99.0%, 99.2%, 99.3%, 99.4%, 99.5% and very particularly preferably 100%, identical to the nucleic acid sequence given in SEQ ID No. 2, and the promoter brings about a transcription frequency of the gene expressed by it which corresponds at least to that of a promoter according to SEQ ID No. 2.

According to a further alternative embodiment, the promoter is one which comprises a nucleic acid sequence which is at least 80% and increasingly preferably at least 81.0%, 82.0%, 83.0%, 84.0%, 85.0%, 86.0%, 87.0%, 88.0%, 89.0%, 90.0%, 91.0%, 92.0%, 93.0%, 94.0%, 95.0%, 96.0%, 97.0%, 98.0%, 99.0%, 99.2%, 99.3%, 99.4%, 99.5% and very particularly preferably 100%, identical to the nucleic acid sequence given in SEQ ID No. 3, and the promoter brings about a transcription frequency of the gene expressed by it which corresponds at least to that of a promoter according to SEQ ID No. 3.

According to another alternative embodiment, the promoter is one which comprises a nucleic acid sequence which is at least 80% and increasingly preferably at least 81.0%, 82.0%, 83.0%, 84.0%, 85.0%, 86.0%, 87.0%, 88.0%, 89.0%, 90.0%, 91.0%, 92.0%, 93.0%, 94.0%, 95.0%, 96.0%, 97.0%, 98.0%, 99.0%, 99.2%, 99.3%, 99.4%, 99.5% and very particularly preferably 100%, identical to the nucleic acid sequence given in SEQ ID No. 4, and the promoter brings about a transcription frequency of the gene expressed by it which corresponds at least to that of a promoter according to SEQ ID No. 4.

In a further alternative embodiment, the promoter has a nucleic acid sequence as described above.

The identity of nucleic acid or amino acid sequences is determined by means of a sequence comparison. Such a comparison is made by assigning similar sequences in the nucleotide sequences or amino acid sequences to one another. This sequence comparison is preferably made on the basis of the BLAST algorithm, which is established in the prior art and customarily used (cf. for example altschul, S. F., Gish, W., Miller, W., Myers, E. W. & Lipman, D. J. (1990) "Basic local alignment search tool." J. Mol. Biol. 215:403-410, and Altschul, Stephan F., Thomas L. Madden, Alejandro A. Schaffer, Jinghui Zhang, Hheng Zhang, Webb Miller, and David J. Lipman (1997): "Gapped BLAST and PSI-BLAST: a new generation of protein database search programs"; Nucleic Acids Res., 25, pp. 3389-3402), and is performed in principle by assigning similar sequences of nucleotides or amino acids in the nucleic acid or amino acid sequences to one another. A tabular assignment of the positions in question is referred to as an alignment. A further algorithm available in the prior art is the FASTA algorithm. Sequence comparisons (alignments), in particular multiple sequence comparisons, are usually generated using computer programs. Frequently used are, for example, the Clustal series (cf. for example Chenna et al. (2003): Multiple sequence alignment with the Clustal series of programs. Nucleic Acid Research 31, 3497-3500), T-Coffee (cf. for example Notredame et al. (2000): T-Coffee: A novel method for multiple sequence alignments. J. Mol. Biol. 302, 205-217) or programs which are based on these programs or algorithms. In the context of the present invention, sequence comparisons and alignments are preferably generated using the computer program Vector NTI® Suite 10.3 (Invitrogen Corporation, 1600 Faraday Avenue, Carlsbad, Calif., USA) using the predefined standard (default) parameters.

Such a comparison reveals the similarity of the compared sequences to one another. It is usually given in percent identity, i.e. the proportion of identical nucleotides or amino acid radicals on the same positions or positions corresponding to one another in an alignment. The more broadly defined term homology takes preserved amino acid substitutions into consideration for amino acid sequences, i.e. amino acids with similar properties since these in most cases exercise similar activities or functions within the protein. Consequently, the similarity of the compared sequences can also be given as percent homology or percent similarity. Identity and/or homology values can be given over entire polypeptides or genes or only over individual regions. Homologous or identical regions of different nucleic acid or amino acid sequences are therefore defined by congruities in the sequences. They often have identical or similar functions. They can be small and comprise only a few nucleotides or amino acids. Such small regions often exercise essential functions for the overall activity of the protein. It may therefore be useful to relate sequence congruities only to individual, possibly small regions. Unless stated otherwise, identity and homology values in the present application, however, refer to the overall length of the nucleic acid or amino acid sequence stated in each case. In the case of proteins, in particular in the case of enzymes and, among these, particularly in the case of proteases, the values also refer to the ripe (mature) protein in each case, unless stated otherwise. Unless indicated otherwise, a sequence viewing for a protein is consequently always directed to the ripe, ready-processed protein, even if the associated gene encodes an immature form which, after translation, is further processed to the ripe form.

The expression construct to be introduced into the microorganism in a method according to the invention also codes for a protein. It consequently comprises a nucleic acid sequence which codes for this protein. Any desired nucleic acid sequence which can be translated into a protein can in principle be used for this purpose. Here, it is the protein which is to be produced with the help of a method according to the invention (target protein). Preferably, it is an enzyme, further preferably an enzyme as described below.

Nucleic acids and expression constructs according to the invention can be generated via methods known per se for modifying nucleic acids. Such methods are presented for example in relevant handbooks, such as that by Fritsch, Sambrook and Maniatis, "Molecular cloning: a laboratory manual", Cold Spring Harbour Laboratory Press, New York, 1989, and known to the person skilled in the art in the field of biotechnology. Examples of such methods are the chemical synthesis or the polymerase chain reaction (PCR), optionally in conjunction with further standard methods in molecular biology and/or chemistry or biochemistry.

The present invention is particularly suitable for the recombinant production of proteins, in particular enzymes. For this, the expression construct is inserted into the microorganism, preferably by means of transformation. In this regard, the incorporation of the particular expression construct or parts thereof preferably takes place via vectors, in particular expression vectors. However, it is also possible for only parts of the expression construct, preferably at least the nucleic acid which codes for the protein, to be introduced into the microorganism in such a way that the finished expression construct is formed only in the microorganism. This can take place for example by means of a vector which enables the gene for the protein in the host cell to be inserted into an already present genetic element such as the chromosome, the chromosomal DNA or other vectors, such that, for example, an endogenous promoter is used for the expression of the gene for the protein. The term introduction comprises the possibility that an expression construct is introduced, preferably transformed, in its entirety into the microorganism, but also the possibility that only part of the expression construct, particularly preferably the nucleic acid which codes for the protein, is introduced, preferably transformed, into the microorganism, and the complete expression construct is formed only in the microorganism. However, in the context of the invention, at least some of the expression construct is always introduced into the microorganism.

Vectors are known to a person skilled in the art of biotechnology. Particularly when used in bacteria, they are specific plasmids, i.e. circular genetic elements. In the context of the present invention, the expression construct is preferably cloned into a vector. The vectors can include for example those which are derived from bacterial plasmids, from viruses or from bacteriophages, or predominantly synthetic vectors or plasmids with elements of highly diverse origin. With the further genetic elements present in each case, vectors are able to become established in the microorganisms over multiple generations as stable units. In the context of the invention, it is unimportant here whether they are established extrachromosomally as separate units or are integrated into the chromosomal DNA. Which of the numerous systems is chosen depends on the individual case. Decisive factors may be, for example, the achievable copy number, the selection systems available, including in particular antibiotic resistances, or the cultivatability of the microorganisms capable of vector uptake.

Expression vectors can furthermore be regulatable by means of changes in the culture conditions, such as, for example, the cell density or the addition of certain compounds. One example of such a compound is the galactose derivative isopropyl-β-D-thiogalactopyranoside (IPTG), which is used as an activator of the bacterial lactose operon (lac operon).

In a further embodiment of the invention, a method according to the invention is one wherein the protein is not naturally present in the microorganism.

In this connection, not naturally present means that the protein is not an endogenous protein or enzyme of the microorganism. The protein can consequently not be expressed in the microorganism by a nucleic acid sequence which is part of the chromosomal DNA of the microorganism in its wild-type form. The protein and/or the nucleic acid sequence coding for it in each case is consequently not present in the wild-type form of the microorganism and/or cannot be isolated therefrom from the wild-type form of the microorganism. Preferably, a protein not present naturally in the microorganism or the nucleic acid sequence coding for it has been specifically introduced into the microorganism with the help of gene-technology methods such that the microorganism has been enriched by the protein or the nucleic acid sequence coding for it. However, a protein can of course be naturally present in another microorganism—relevant to the discussion is exclusively the microorganism used in the method.

In a further embodiment of the invention, the method is one wherein the protein is an enzyme, in particular an acidic cellulase, alpha-amylase, alpha-acetodecarboxylase, aminopetidase, amylase, arabanase, beta-glucanase, beta-glucosidase, beta-mannosidase, carageenase, carbohydrase, catalase, cellobiose-oxidase, cellulase, chymosin, endo-1,3-beta-glucanase, endo-1,3(4)-beta-glucanase, endo-1,4-beta-xylanase, endopeptidase, esterase, exopeptidase, G4-amylase, glucoamylase, glucose oxidase, glucosidase, glycolipase, hemicellulase, laccase, lipase, lysophospholipase, maltogenic amylase, mannanase, neutral protease, nuclease, oxidase, oxidoreductase, pectate lyase, pectinase, pectin esterase, pentosanase, perhydrolase, phospholipase, phytase, polygalacturonase, protease, proteinase, pullulanase, rennet enzyme, rhamnogalacturonase, subtilisin, tannase, transferase, transglutaminase, xanthanase, xylanase, xyloglucanase or mixtures thereof. Very particularly preferably the protein is a protease. In particularly advantageous embodiments of a method according to the invention, the protease to be produced (=target protease) is simultaneously also involved in the hydrolysis of the protein substrate for the microorganism and can advantageously bring about a further improved digestion of substrate protein. Consequently, improved nutrient conditions are then available to the microorganism.

For example, using a method according to the invention it is possible to advantageously produce the enzymes specified below.

Among the proteases, subtilisins are preferred. Examples thereof are the subtilisins BPN' and Carlsberg, the protease PB92, the subtilisins 147 and 309, the alkaline protease from *Bacillus lentus*, subtilisin DY and the enzymes to be assigned to the subtilases but no longer to the subtilisins in the narrower sense, these being thermitase, proteinase K and the protease TW3 and TW7. Subtilisin Carlsberg is available in a further developed form under the trade name Alcalase® from Novozymes A/S, Bagsværd, Denmark. The subtilisins 147 and 309 are sold by Novozymes under the trade names Esperase®, or Savinase®. Derived from the proteases from *Bacillus lentus* DSM 5483 are the protease variants listed under the name BLAP®. Further preferred proteases are also for example the enzymes listed under the name PUR. Further proteases are also the enzymes available under the trade names Durazym®, Relase®, Everlase®, Nafizym®, Natalase®, Kannase® and Ovozyme® from Novozymes, those available under the trade names Purafect®, Purafect® OxP, Purafect® Prime, Excellase® and Properase® from Genencor/Danisco, that available under the trade name Protosol® from Advanced Biochemicals Ltd., Thane, India, that available under the trade name Wuxi® from Wuxi Snyder Bioproducts Ltd., China, those available under the trade names Proleather® and Protease P® from Amano Pharmaceuticals Ltd., Nagoya, Japan, and that available under the name Proteinase K-16 from Kao Corp., Tokyo, Japan. Preference is also given to the proteases from *Bacillus gibsonii* and *Bacillus pumilus*, which are disclosed in the international patent applications WO2008/086916 and WO2007/131656.

Examples of amylases are the α-amylases from *Bacillus licheniformis*, from *Bacillus amyloliquefaciens* or from *Bacillus stearothermophilus*, and in particular also their further developments improved for use in detergents or cleaners. The enzyme from *Bacillus licheniformis* is available from Novozymes under the name Termamyl® and from Danisco/Genencor under the name Purastar® ST. Further-development products of this α-amylase are available from Novozymes under the trade names Duramyl® and Termamyl® ultra, from Danisco/Genencor under the name Purastar®OxAm and from Daiwa Seiko Inc., Tokyo, Japan, as Keistase®. The α-amylase from *Bacillus amyloliquefaciens* is sold by Novozymes under the name BAN®, and derived variants of the α-amylase from *Bacillus stearothermophilus* under the name BSG® and Novamyl®, likewise from Novozymes. Furthermore, the α-amylase from *Bacillus* sp. A 7-7 (DSM 12368) and the cyclodextrin-glucanotransferase (CGTase) from *Bacillus agaradherens* (DSM 9948) are to be mentioned. It is likewise possible to use fusion products of all of the specified molecules. Moreover, the further developments of the α-amylase from *Aspergillus niger* and *A. oryzae* available under the trade name Fungamyl® from Novozymes are suitable. Further advantageous commercial products are for example the amylase Powerase® from Danisco/Genencor and the amylases Amylase-LT®, Stainzyme® and Stainzyme Plus®, the latter from Novozymes. Variants of these enzymes available by point mutations can also be produced according to the invention. Further preferred amylases are disclosed in the international laid-open specifications WO 00/60060, WO 03/002711, WO 03/054177 and WO 07/079,938, to the disclosure of which reference is therefore expressly made and/or whose disclosure in this respect is therefore expressly incorporated into the present patent application. Amylases to be prepared according to the invention are also preferably α-amylases.

Examples of lipases or cutinases are the lipases available originally from *Humicola lanuginosa* (*Thermomyces lanuginosus*), or further-developed ones, in particular those with the amino acid substitution D96L. They are sold for example by Novozymes under the trade names Lipolase®, Lipolase® Ultra, LipoPrime®, Lipozyme® and Lipex®. Furthermore, it is for example possible to prepare the cutinases which have been isolated originally from *Fusarium solani pisi* and *Humicola insolens*. From Danisco/Genencor, for example, the lipases or cutinases can be prepared whose starting enzymes have originally been isolated from *Pseudomonas mendocina* and *Fusarium solanii*. Further important commercial products are the preparations M1 Lipase® and Lipomax® sold originally by Gist-Brocades (interim Danisco/Genencor) and the enzymes sold by Meito Sangyo KK, Japan, under the names Lipase MY-30®, Lipase OF® and Lipase PL®, as well as the product Lumafast® from Danisco/Genencor.

Examples of cellulases (endoglucanases, EG) comprise sequences of the fungal, endoglucanase(EG)-rich cellulase preparation or further developments thereof which are supplied by Novozymes under the trade name Celluzyme®. The products Endolase® and Carezyme®, likewise available from Novozymes, are based on the 50 kD-EG, or the 43 kD-EG from *Humicola insolens* DSM 1800. Further commercial products from this company that can be prepared are Cellusoft®, Renozyme® and Celluclean®. It is furthermore possible to prepare for example cellulases, which are available from AB Enzymes, Finland, under the trade names Ecostone® and Biotouch®, and which are based at least in part on the 20 kD-EG from Melanocarpus. Further cellulases from AB Enzymes are Econase® and Ecopulp®. Further suitable cellulases are from *Bacillus* sp. CBS 670.93 and CBS 669.93, where that from *Bacillus* sp. CBS 670.93 is available from Danisco/Genencor under the trade name Puradax®. Further commercial products from Danisco/Genencor that can be prepared are "Genencor detergent cellulase L" and IndiAge® Neutra.

Variants of these enzymes available as a result of point mutations can also be prepared according to the invention. Particularly preferred cellulases are *Thielavia terrestris* cellulase variants which are disclosed in the international laid-open specification WO 98/12307, cellulases from Melanocarpus, in particular Melanocarpus albomyces, which are disclosed in the international laid-open specification WO 97/14804, cellulases of the EGIII type from *Trichoderma reesei*, which are disclosed in the European patent application EP 1 305 432, and variants available therefrom, in particular those which are disclosed in the European patent applications EP 1240525 and EP 1305432, as well as cellulases which are disclosed in the international laid-open specifications WO 1992006165, WO 96/29397 and WO 02/099091. Reference is therefore expressly made to their respective disclosure and/or their disclosure content in this regard is therefore expressly incorporated into the present patent application.

In addition, further enzymes can be prepared which are grouped under the term hemicellulases. These include for example mannanases, xanthanlyases, xanthanases, pectin lyases (=pectinases), pectin esterases, pectate lyases, xyloglucanases, xylanases, pullulanases and β-glucanases. Enzymes suitable in this respect are available for example under the names Gamanase®, Pektinex AR® and Pectaway® from Novozymes, under the name Rohapec® B1L from AB Enzymes or under the name Pyrolase® from Diversa Corp., San Diego, Calif., USA. The β-glucanase obtained from *Bacillus subtilis* is available under the name Cereflo® from Novozymes. Hemicellulases particularly preferred according to the invention are mannanases which are sold for example under the trade names Mannaway® from Novozymes or Purabrite® from Genencor.

Furthermore, oxidoreductases, for example oxidases, oxygenases, catalases, peroxidases, such as halo-, chloro-, bromo-, lignin-, glucose or manganese peroxidases, dioxygenases or laccases (phenol oxidases, polyphenol oxidases) can also be prepared. Suitable commercial products to be mentioned are Denilite® 1 and 2 from Novozymes. Further enzymes are disclosed in the international patent applications WO 98/45398, WO 2005/056782, WO 2004/058961 and WO 2005/124012.

In a further embodiment of the invention, the method is one wherein the microorganism is *Bacillus pumilus* DSM 14395. This strain was deposited on Mar. 1, 2001 at the DSMZ (DSMZ—Deutsche Sammlung von Mikroorganismen and Zellkulturen GmbH, Inhoffenstraβe 7 B, 38124 Braunschweig, Germany) and has been identified by the DSMZ as a *Bacillus pumilus* strain (DSM ID 01-197). As the examples in the present patent application show, very good product yields are achieved with this strain in microbial fermentations.

In a further embodiment of the invention, the strain to be used in a method according to the invention is genetically modified. As a result of the genetic modification, the product yield is advantageously further increased or a property of the product is advantageously modified. Product is to be understood here as meaning the expressed protein which is present in the fermentation medium. For example, its odor is reduced, its color is attenuated and/or the product is clarified (i.e. less cloudy) or its density is reduced. Genetic modification in this respect is not intended to mean the introduction of the expression construct as per method step (a). Rather, the microorganism of the species *Bacillus pumilus* to be used in the method according to the invention has already been genetically modified, and specifically before the expression construct as per method step (a) is introduced into the microorganism. Preferably, the presence of the genetic modification is ascertained in comparison with the *Bacillus pumilus* wild type, in particular *Bacillus pumilus* DSM 14395. The genetic modification contemplated in this regard is substitutions, insertions and/or deletions. Advantageously, the genetic modification brings about the functional change, for example the functional deactivation, of a gene in the microorganism. The functional change, for example the functional deactivation, of the gene then in turn brings about an increased and/or improved production of the protein and therefore an improved product yield and/or the obtainment of a product with one or more improved properties. Functional deactivation is to be understood as meaning that the gene product(s) coded by this gene is/are no longer formed or is/are formed in a biologically inactive form such that it/they can no longer exercise its function(s) in the microorganism. In this regard, a functional deactivation of a gene can in particular also take place by completely or partially replacing it by an alternative gene. This alternative gene can then be expressed instead of the gene originally present. Consequently, the originally present gene was functionally deactivated; instead, the alternative gene is expressed and the functional change is brought about as a result. The alternative gene can be a gene related to the original gene (more than 50% identity to the original gene) or a gene not related to the original gene (50% or less identity to the original gene). For example, the alternative gene can be introduced into the coding sequence of the original gene by means of insertion. As a result, the original gene is functionally deactivated and instead the alternative gene is expressed. The genetic modification can be present either in the sequence coding for the gene product or else in a gene-regulatory sequence belonging to the gene.

Microorganisms to be used according to the invention can be modified for example as regards their demands on the culture conditions, be modified as regards their mobility behavior, be modified as regards their sporulation capability, be modified as regards a certain metabolic pathway—for example in order to suppress the formation of malodors during fermentation—, or else have other or additional selection markers.

Genetically modifiable in this regard are all genes in the *Bacillus pumilus* strain to be used in a method according to the invention to which there is an equivalent in the *Bacillus pumilus* genome which is disclosed in the publication by Gioia et al., PLoS ONE, 9: e928 (2007). This publication describes the first completely sequenced *Bacillus pumilus* genome. Reference is expressly made to this reference and this is incorporated into the disclosure content of the present patent application.

Furthermore, all genes in the *Bacillus pumilus* strain to be used in a method according to the invention to which there is an equivalent in one or more of the genomes of the microorganisms given below can be genetically modified:

Agrobacterium radiobacter K84, Agrobacterium tumefaciens str. C58, Agrobacterium vitis S4, Arcobacter butzleri ED-1, Arcobacter nitrofigilis DSM 7299, Arcobacter sp. L, Aromatoleum aromaticum EbN1, Arthrobacter aurescens TC1, Arthrobacter chlorophenolicus A6, Arthrobacter phenanthrenivorans Sphe3, Arthrobacter sp. FB24, Bacillus amyloliquefaciens DSM 7, Bacillus amyloliquefaciens FZB42, Bacillus anthracis str. Ames, Bacillus atrophaeus 1942, Bacillus cellulosilyticus DSM 2522, Bacillus cereus ATCC 10987, Bacillus cereus ATCC 14579, Bacillus cereus B4264, Bacillus clausii KSM-K16, Bacillus coagulans 36D1, Bacillus cytotoxicus NVH 391-98, Bacillus halodurans C-125, Bacillus licheniformis ATCC 14580, Bacillus megaterium DSM 319, Bacillus pseudofirmus OF4, Bacillus pseudomycoides DSM 12442 (305 parts in a CON entry), Bacillus pumilus SAFR-032, Bacillus selenitireducens MLS10, Bacillus subtilis BSn5, Bacillus subtilis subsp. spizizenii str. W23, Bacillus subtilis subsp. spizizenii TU-B-10, Bacillus subtilis subsp. subtilis RO-NN-1, Bacillus subtilis subsp. subtilis str. 168, Bacillus thuringiensis BMB1713, Bacillus thuringiensis serovar konkukian str. 97-27T, Bacillus thuringiensis serovar thuringiensis str. T01001, Bacillus tusciae DSM 2912, Bacillus weihenstephanensis KBAB4, Bifidobacterium adolescentis ATCC 15703, Bifidobacterium animalis subsp. lactis V9, Bifidobacterium bifidum PRL2010, Bifidobacterium breve UCC2003, Bifidobacterium dentium Bd1, Bifidobacterium longum DJO10A, Bifidobacterium longum NCC27051, Bifidobacterium longum subsp. infantis ATCC 15697, Bradyrhizobium sp. ORS 278, Brevibacillus brevis NBRC 100599, Corynebacterium aurimucosum ATCC 700975, Corynebacterium diphtheriae NCTC 13129, Corynebacterium efficiens YS-314, Corynebacterium glutamicum ATCC 13032, Corynebacterium glutamicum R, Corynebacterium jeikeium K411, Corynebacterium kroppenstedtii DSM 44385, Corynebacterium pseudotuberculosis FRC41, Corynebacterium resistens DSM 45100, Corynebacterium ulcerans BR-AD22, Corynebacterium urealyticum DSM 7109, Corynebacterium variabile DSM 44702, Desulfovibrio aespoeensis Aspo-2, Desulfovibrio alaskensis G20, Desulfovibrio desulfuricans subsp. desulfuricans str. ATCC 27774, Desulfovibrio magneticus RS-1, Desulfovibrio salexigens DSM 2638, Desulfovibrio vulgaris RCH1, Desulfovibrio vulgaris str. Miyazaki F, Desulfurobacterium thermolithotrophum DSM 11699, Enterobacter aerogenes KCTC 2190, Enterobacter asburiae LF7a, Enterobacter cloacae subsp. cloacae ATCC 13047 Enterobacter sp. 638 Escherichia coli 536, Escherichia coli APEC O1, Escherichia coli CFT073, Escherichia coli O103:H2 str. 12009, Escherichia coli SE11, Escherichia coli SE15-, Escherichia fergusonii ATCC 35469T chromosome, Ethanoligenens harbinense YUAN-3, Eubacterium cylindroides T2-87 draft, Eubacterium eligens ATCC 27750, Eubacterium limosum KIST612, Eubacterium rectale M104/1 draft, Eubacterium siraeum 70/3 draft, Exiguobacterium sibiricum 255-15, Exiguobacterium sp. AT1b, Flavobacteriaceae bacterium 3519-10, Flavobacterium branchiophilum FL-15, Flavobacterium johnsoniae UW101, Flavobacterium psychrophilum JIP02/86, Geobacillus kaustophilus HTA426, Geobacillus sp. C56-T3, Geobacillus sp. WCH70, Geobacillus sp. Y4.1 MC1, Geobacillus sp. Y412MC52 Geobacillus sp. Y412MC61, plasmid pGYMC6101, Geobacillus thermodenitrificans NG80-2, Geobacillus thermoglucosidasius C56-YS93, Geobacter bemidjiensis Bem Geobacter lovleyi SZ, Geobacter metallireducens GS-15 Geobacter sp. FRC-32, Geobacter sp. M18, Geobacter sp. M21, Geobacter sulfurreducens PCA, Geobacter uraniireducens Rf4, Gloeobacter violaceus PCC 74212, Gluconacetobacter diazotrophicus PAl 5, ATCC 49037, Gluconacetobacter xylinus NBRC 3288, Gluconobacter oxydans 621H, Hydrogenobaculum sp. Y04AAS1, Lactobacillus acidophilus 30SC, Lactobacillus amylovorus GRL 1112, Lactobacillus brevis ATCC 367, Lactobacillus buchneri NRRL B-30929, Lactobacillus casei ATCC 334, Lactobacillus casei BD-II, Lactobacillus casei BL23, Lactobacillus casei LC2W, Lactobacillus crispatus ST10, Lactobacillus delbrueckii subsp. bulgaricus ND02, Lactobacillus fermentum CECT 5716, Lactobacillus gasseri ATCC 33323, Lactobacillus helveticus H10, Lactobacillus johnsonii NCC 533, Lactobacillus kefiranofaciens ZW3, Lactobacillus plantarum WCFS1, Lactobacillus reuteri SD2112, Lactobacillus rhamnosus GG, Lactobacillus rhamnosus GG ATCC 53103, Lactobacillus ruminis ATCC 27782, Lactobacillus sakei subsp. sakei 23K, Lactobacillus salivarius CECT 5713, Lactobacillus sanfranciscensis TMW 1.1304, Mannheimia succiniciproducens MBEL55E, Mycobacterium abscessus chromosome, Mycobacterium africanum GM041182, Mycobacterium avium 104, Mycobacterium bovis BCG str. Tokyo 172, Mycobacterium canettii CIPT 140010059, Mycobacterium gilvum PYR-GCK, Mycobacterium marinum M, Mycobacterium smegmatis str. MC2 155, Mycobacterium sp. JDM601, Mycobacterium sp. JLS, Mycobacterium sp. KMS, Mycobacterium sp. MCS, Mycobacterium sp. Spyr1, Mycobacterium vanbaalenii PYR-1, Pseudomonas aeruginosa NCGM2.S17, Pseudomonas brassicacearum subsp. brassicacearum NFM421, Pseudomonas entomophila L48 chromosome, Pseudomonas fluorescens Pf-5, Pseudomonas fulva 12-X, Pseudomonas mendocina NK-01, Pseudomonas putida KT2440+, Pseudomonas syringae pv. phaseolicola 1448A, Pseudomonas stutzeri DSM 4166, Pseudomonas syringae pv. syringae B728a+, Pseudomonas syringae pv. tomato str. DC3000/, Stenotrophomonas maltophilia K279a strain K279a, Streptobacillus moniliformis DSM 12112, Streptomyces avermitilis MA-4680, Streptomyces bingchenggensis BCW-1, Streptomyces cattleya NRRL 8057 main chromosome, Streptomyces clavuligerus ATCC 27064, Streptomyces coelicolor, Streptomyces flavogriseus ATCC 33331, Streptomyces griseus subsp. griseus NBRC 13350, Streptomyces scabiei 87.22, Streptomyces sp. SirexAA-E, Streptomyces venezuelae ATCC 10712, Streptomyces violaceusniger Tu 4113, Sulfobacillus acidophilus TPY, Thermobifida fusca YX, Thermotoga lettingae TMO, Thermotoga maritima MSB8, Thermotoga naphthophila RKU-10, Thermotoga neapolitana DSM 4359, Thermotoga petrophila RKU-1, Thermotoga sp. RQ2, Thermovibrio ammonificans HB-1, Thermus thermophilus HB27, Xanthomonas albilineans, Xanthomonas axonopodis pv. citrumelo F1, Xanthomonas axonopodis pv. citri str. 306/, Xanthomonas campestris pv. campestris str. 8004, Xanthomonas euvesicatoria, Xanthomonas oryzae pv. oryzae.

Besides the cited publication, the modifiable genes, in particular the sequences thereof, are also available in publically accessible databases, for example in the KEGG (Kyoto Encyclopedia of Genes and Genomes) database under www.genome.jp/kegg or in the databases of the NCBI (National Center for Biotechnology Information, U.S. National Library of Medicine, 8600 Rockville Pike, Bethesda, Md. 20894, USA) under www.ncbi.nlm.nih.gov. The KEGG database has been developed since 1995 by the laboratories under Kanehisa et al. of the "Kyoto University Bioinformatics Center" and of the "Human Genome Center of the University of Tokyo". Besides individual genes, these databases also comprise information and sequences of entire genomes or large parts of the genome of various microorganisms.

A genetic equivalent in the context of the present patent application is notable firstly for the highest possible sequence homology between the gene of the *Bacillus pumilus* strain to be used according to the invention and the gene of the *Bacillus pumilus* strain published by Gioia et al. and/or the gene of the microorganism given above. Secondly, a genetic equivalent is notable for a similar type of function, i.e. the mutually corresponding genes of the *Bacillus pumilus* strain to be used according to the invention and of the *Bacillus pumilus* strain published by Gioia et al. and/or of the microorganism given above have a similar type of function in the respective microorganism.

With this gene and/or genome information it is possible to identify the respective gene in the *Bacillus pumilus* strain to be used in a method according to the invention by reference to sequence comparisons. Based on the genetic information, in particular the sequence information, from the genome of the *Bacillus pumilus* strain published by Gioia et al. and/or from the genome of a microorganism given above, the person skilled in the art can ascertain, by sequence comparison and/or molecular biological standard methodology, the nucleic acid sequence with the highest sequence agreement in the genome of the *Bacillus pumilus* strain which is to be genetically modified and then used in the method according to the invention. Confirmation of a similar type of function, i.e. a functional equivalence, can be made by comparative experiments with the respective microorganisms in which in each case the gene compared on the basis of the sequence comparison is modified (preferably functionally deactivated) in the same way and it is observed whether the same type of modifications, in particular phenotypic modifications, arise in both microorganisms. If, for example, the modification, in particular the functional deactivation, of the gene in question in the *Bacillus pumilus* strain published by Gioia et al. and/or in the microorganism given above is associated with a change in metabolic activity, the mobility or the sporulation behavior and if a corresponding change in the *Bacillus pumilus* strain to be used and to be modified according to the invention is observed, then this is to be considered as confirmation of the correct assignment. Corresponding methods are standard in the field of genetics, in particular the genetics of microorganisms, and are known comprehensively to the skilled person in this field.

In a particularly preferred embodiment, the microorganism is sporulation-inhibited. This is preferably achieved by functionally deactivating its gene spoIV (yqfD) or its genetic equivalent, in particular by means of deleting the gene spoIV (yqfD) or its genetic equivalent or parts thereof. It has been found that with a *Bacillus pumilus* strain sporulation-inhibited in this way, a particularly high product yield is achieved in a method according to the invention.

The microorganisms used in methods according to the invention can be cultivated and fermented in the usual way, for example in discontinuous or continuous systems. In the first case, a suitable nutrient medium is inoculated with the microorganisms and the protein is harvested from the medium after a period to be determined experimentally. Continuous fermentations are marked by achieving a flow equilibrium in which, over a comparatively long period, cells partly die off but also regrow and at the same time the protein formed can be removed from the medium.

Methods according to the invention are preferably fermentation methods. Fermentation methods are known per se from the prior art and constitute the actual large-scale industrial production step, usually followed by a suitable purification method of the protein produced. All fermentation methods which are based on a method according to the invention for producing a protein constitute embodiments of a method according to the invention.

Fermentation methods which are characterized in that the fermentation is carried out via a feed strategy are in particular contemplated. Herein, the media constituents, which are used up by the progressing cultivation, are fed in. As a result, considerable increases both in the cell density as well as in the cell mass or dry mass can be achieved. Furthermore, the fermentation can also be designed such that undesired metabolic products are filtered out or neutralized by adding buffer or counterions suitable in each case.

The protein produced can be harvested from the fermentation medium. Such a fermentation method is preferred over an isolation of the protein from the microorganism, i.e. a product preparation from the cell mass (dry mass). This can be achieved for example by means of the provision of suitable secretion markers and/or mechanisms and/or transport systems so that the microorganisms secrete the protein into the fermentation medium. Without secretion, the isolation of the protein can alternatively take place from the host cell, i.e. a purification of the same from the cell mass, for example by precipitation with ammonium sulfate or ethanol, or by chromatographic purification.

The invention further provides a microorganism which is obtainable by a method which comprises the following method steps:

(a) introducing an expression construct into a microorganism which comprises a promoter and a nucleic acid coding for the protein;

(b) expression of the protein in the microorganism, where the microorganism belongs to the species *Bacillus pumilus*.

These are accordingly all microorganisms which can be the subject of a method according to the invention. All material facts, subjects and embodiments which are described for methods according to the invention can also be applied to this inventive subject matter. Consequently, at this point, reference is expressly made to the disclosure at the corresponding point, with the indication that this disclosure also applies to the microorganisms according to the invention.

Particularly preferred embodiments of microorganisms according to the invention are ones wherein (a) the promoter comprises a nucleic acid sequence which is selected from

- (i) nucleic acid sequence which is at least 80% and increasingly preferably at least 81.0%, 82.0%, 83.0%, 84.0%, 85.0%, 86.0%, 87.0%, 88.0%, 89.0%, 90.0%, 91.0%, 92.0%, 93.0%, 94.0%, 95.0%, 96.0%, 97.0%, 98.0%, 99.0%, 99.2%, 99.3%, 99.4%, 99.5% and very particularly preferably 100%, identical to the nucleic acid sequence given in SEQ ID No. 1;
- (ii) nucleic acid sequence which is at least 80% and increasingly preferably at least 81.0%, 82.0%, 83.0%, 84.0%, 85.0%, 86.0%, 87.0%, 88.0%, 89.0%, 90.0%, 91.0%, 92.0%, 93.0%, 94.0%, 95.0%, 96.0%, 97.0%, 98.0%, 99.0%, 99.2%, 99.3%, 99.4%, 99.5% and very particularly preferably 100%, identical to the nucleic acid sequence given in SEQ ID No. 2;
- (iii) nucleic acid sequence which is at least 80% and increasingly preferably at least 81.0%, 82.0%, 83.0%, 84.0%, 85.0%, 86.0%, 87.0%, 88.0%, 89.0%, 90.0%, 91.0%, 92.0%, 93.0%, 94.0%, 95.0%, 96.0%, 97.0%, 98.0%, 99.0%, 99.2%, 99.3%, 99.4%, 99.5% and very particularly preferably 100%, identical to the nucleic acid sequence given in SEQ ID No. 3;
(iv) nucleic acid sequence which is at least 80% and increasingly preferably at least 81.0%, 82.0%, 83.0%, 84.0%, 85.0%, 86.0%, 87.0%, 88.0%, 89.0%, 90.0%, 91.0%, 92.0%, 93.0%, 94.0%, 95.0%, 96.0%, 97.0%, 98.0%, 99.0%, 99.2%, 99.3%, 99.4%, 99.5% and very particularly preferably 100%, identical to the nucleic acid sequence given in SEQ ID No. 4, and/or
(b) the protein is not naturally present in the microorganism, and/or
(c) the protein is an enzyme, in particular an acidic cellulase, alpha-amylase, alpha-acetodecarboxylase, aminopetidase, amylase, arabanase, beta-glucanase, beta-glucosidase, beta-mannosidase, carageenase, carbohydrase, catalase, cellobiose-oxidase, cellulase, chymosin, endo-1,3-beta-glucanase, endo-1,3(4)-beta-glucanase, endo-1,4-beta-xylanase, endopeptidase, esterase, exopeptidase, G4-amylase, glucoamylase, glucose oxidase, glucosidase, glycolipase, hemicellulase, laccase, lipase, lysophospholipase, maltogenic amylase, mannanase, neutral protease, nuclease, oxidase, oxidoreductase, pectate lyase, pectinase, pectin esterase, pentosanase, perhydrolase, phospholipase, phytase, polygalacturonase, protease, proteinase, pullulanase, rennet enzyme, rhamnogalacturonase, subtilisin, tannase, transferase, transglutaminase, xanthanase, xylanase, xyloglucanase, preferably protease or alpha-amylase, or mixtures thereof, and/or
(d) the microorganism is *Bacillus pumilus* DSM 14395, and/or
(e) the microorganism is sporulation-inhibited, preferably as a result of modifying the gene spoIV (yqfD), in particular as a result of deleting the gene spoIV (yqfD) or parts thereof, and/or
(f) the microorganism is genetically modified.

A very particularly preferred embodiment of microorganisms according to the invention is one wherein
(a) the promoter comprises a nucleic acid sequence which is selected from
(i) nucleic acid sequence which is at least 80% and increasingly preferably at least 81.0%, 82.0%, 83.0%, 84.0%, 85.0%, 86.0%, 87.0%, 88.0%, 89.0%, 90.0%, 91.0%, 92.0%, 93.0%, 94.0%, 95.0%, 96.0%, 97.0%, 98.0%, 99.0%, 99.2%, 99.3%, 99.4%, 99.5% and very particularly preferably 100%, identical to the nucleic acid sequence given in SEQ ID No. 1;
(ii) nucleic acid sequence which is at least 80% and increasingly preferably at least 81.0%, 82.0%, 83.0%, 84.0%, 85.0%, 86.0%, 87.0%, 88.0%, 89.0%, 90.0%, 91.0%, 92.0%, 93.0%, 94.0%, 95.0%, 96.0%, 97.0%, 98.0%, 99.0%, 99.2%, 99.3%, 99.4%, 99.5% and very particularly preferably 100%, identical to the nucleic acid sequence given in SEQ ID No. 2;

and/or
(b) the protein is not naturally present in the microorganism, and/or
(c) the protein is a protease, preferably a subtilisin, or an alpha-amylase
and/or
(d) the microorganism is *Bacillus pumilus* DSM 14395, and/or
(e) the microorganism is sporulation-inhibited, preferably as a result of modifying the gene spoIV (yqfD), in particular as a result of deleting the gene spoIV (yqfD) or parts thereof, and/or
(f) the microorganism is genetically modified.

A further very particularly preferred embodiment of microorganisms according to the invention is one wherein
(a) the promoter comprises a nucleic acid sequence which is selected from
(i) nucleic acid sequence which is at least 80% and increasingly preferably at least 81.0%, 82.0%, 83.0%, 84.0%, 85.0%, 86.0%, 87.0%, 88.0%, 89.0%, 90.0%, 91.0%, 92.0%, 93.0%, 94.0%, 95.0%, 96.0%, 97.0%, 98.0%, 99.0%, 99.2%, 99.3%, 99.4%, 99.5% and very particularly preferably 100%, identical to the nucleic acid sequence given in SEQ ID No. 1;
(ii) nucleic acid sequence which is at least 80% and increasingly preferably at least 81.0%, 82.0%, 83.0%, 84.0%, 85.0%, 86.0%, 87.0%, 88.0%, 89.0%, 90.0%, 91.0%, 92.0%, 93.0%, 94.0%, 95.0%, 96.0%, 97.0%, 98.0%, 99.0%, 99.2%, 99.3%, 99.4%, 99.5% and very particularly preferably 100%, identical to the nucleic acid sequence given in SEQ ID No. 2;
(iii) nucleic acid sequence which is at least 80% and increasingly preferably at least 81.0%, 82.0%, 83.0%, 84.0%, 85.0%, 86.0%, 87.0%, 88.0%, 89.0%, 90.0%, 91.0%, 92.0%, 93.0%, 94.0%, 95.0%, 96.0%, 97.0%, 98.0%, 99.0%, 99.2%, 99.3%, 99.4%, 99.5% and very particularly preferably 100%, identical to the nucleic acid sequence given in SEQ ID No. 3;
(iv) nucleic acid sequence which is at least 80% and increasingly preferably at least 81.0%, 82.0%, 83.0%, 84.0%, 85.0%, 86.0%, 87.0%, 88.0%, 89.0%, 90.0%, 91.0%, 92.0%, 93.0%, 94.0%, 95.0%, 96.0%, 97.0%, 98.0%, 99.0%, 99.2%, 99.3%, 99.4%, 99.5% and very particularly preferably 100%, identical to the nucleic acid sequence given in SEQ ID No. 4, and/or
(b) the protein is not naturally present in the microorganism, and/or
(c) the protein is an alpha-amylase
and/or
(d) the microorganism is *Bacillus pumilus* DSM 14395, and/or
(e) the microorganism is sporulation-inhibited, preferably as a result of modifying the gene spoIV (yqfD), in particular as a result of deleting the gene spoIV (yqfD) or parts thereof, and/or
(f) the microorganism is genetically modified.

An embodiment of microorganisms according to the invention that is particularly preferred to the highest extent is one wherein
(a) the promoter comprises a nucleic acid sequence which is at least 80% and increasingly preferably at least 81.0%, 82.0%, 83.0%, 84.0%, 85.0%, 86.0%, 87.0%, 88.0%, 89.0%, 90.0%, 91.0%, 92.0%, 93.0%, 94.0%, 95.0%, 96.0%, 97.0%, 98.0%, 99.0%, 99.2%, 99.3%, 99.4%, 99.5% and very particularly preferably 100%, identical to the nucleic acid sequence given in SEQ ID No. 3;
and/or
(b) the protein is not naturally present in the microorganism, and/or
(c) the protein is an alpha-amylase
and/or
(d) the microorganism is *Bacillus pumilus* DSM 14395, and/or (e) the microorganism is sporulation-inhibited, preferably by modifying the gene spoIV (yqfD), in particular by deleting the gene spoIV (yqfD) or parts thereof, and/or
(f) the microorganism is genetically modified.

A further embodiment of microorganisms according to the invention that is particularly preferred to the highest extent is one wherein
(a) the promoter comprises a nucleic acid sequence which is at least 80% and increasingly preferably at least 81.0%, 82.0%, 83.0%, 84.0%, 85.0%, 86.0%, 87.0%, 88.0%, 89.0%, 90.0%, 91.0%, 92.0%, 93.0%, 94.0%, 95.0%, 96.0%, 97.0%, 98.0%, 99.0%, 99.2%, 99.3%, 99.4%, 99.5% and very particularly preferably 100%, identical to the nucleic acid sequence given in SEQ ID No. 1;
and/or
(b) the protein is not naturally present in the microorganism, and/or
(c) the protein is an alpha-amylase
and/or
(d) the microorganism is Bacillus pumilus DSM 14395, and/or
(e) the microorganism is sporulation-inhibited, preferably by modifying the gene spoIV (yqfD), in particular by deleting the gene spoIV (yqfD) or parts thereof, and/or
(f) the microorganism is genetically modified.

An embodiment of microorganisms according to the invention that is particularly preferred to the highest extent is one wherein
(a) the promoter comprises a nucleic acid sequence which is at least 80% and increasingly preferably at least 81.0%, 82.0%, 83.0%, 84.0%, 85.0%, 86.0%, 87.0%, 88.0%, 89.0%, 90.0%, 91.0%, 92.0%, 93.0%, 94.0%, 95.0%, 96.0%, 97.0%, 98.0%, 99.0%, 99.2%, 99.3%, 99.4%, 99.5% and very particularly preferably 100%, identical to the nucleic acid sequence given in SEQ ID No. 2;
and/or
(b) the protein is not naturally present in the microorganism, and/or
(c) the protein is an alpha-amylase
and/or
(d) the microorganism is Bacillus pumilus DSM 14395, and/or
(e) the microorganism is sporulation-inhibited, preferably by modifying the gene spoIV (yqfD), in particular by deleting the gene spoIV (yqfD) or parts thereof, and/or
(f) the microorganism is genetically modified.

Microorganisms according to the invention are advantageously used in methods according to the invention in order to produce a protein. Consequently, the invention further accordingly provides the use of a microorganism according to the invention for producing a protein, in particular an enzyme.

All material facts, subjects and embodiments which are described for methods or microorganisms according to the invention can also be applied to this inventive subject matter. Consequently, at this point, reference is made expressly to the disclosure at the corresponding point, with the indication that this disclosure also applies to the uses according to the invention.

EXAMPLES

All of the molecular biological working steps follow standard methods as given for example in the handbook from Fritsch, Sambrook and Maniatis "Molecular cloning: a laboratory manual", Cold Spring Harbour Laboratory Press, New York, 1989, or comparable relevant works. Enzymes, kits and instruments were used in accordance with the instructions from the respective manufacturers.

Example 1

Comparison of the Fermentative Production of a Protease (Target Protein) with Bacillus pumilus and Bacillus licheniformis Three different expression plasmids as given below, which in each case comprise a gene coding for a protease (target protein) as well as a functional promoter, were transformed both in a Bacillus licheniformis strain as well as in a Bacillus pumilus strain. The transformed strains were used for the fermentative protease production. The Bacillus licheniformis strain used is disclosed in the international patent application WO 91/02792. The Bacillus pumilus strain used was Bacillus pumilus DSM 14395, in which the gene spoIV (yqfD) has been functionally deactivated by means of a deletion. The promoters used were nucleic acid sequences as per SEQ ID No. 1 and SEQ ID No. 2. The promoter is arranged in the respective expression plasmids in each case 5' upstream of the nucleic acid sequence which codes for the protease. The following plasmids were used (table 1):

TABLE 1

| Plasmid No. | Promoter | Protease gene |
|---|---|---|
| 1 | SEQ ID No. 1 | coding for the variant F49 as per WO 95/23221 |
| 2 | SEQ ID No. 1 | coding for the variant F49 as per WO 95/23221 |
| 3 | SEQ ID No. 2 | coding for the variant F49 as per WO 95/23221 |

Following the transformation of the expression plasmids into the respective microorganisms, the resulting production strains were used in a standard fermentation method in a 2 liter laboratory fermenter (48 h culture time) and the resulting protease activities were determined via the release of the chromophore para-nitroaniline (pNA) from the substrate suc-L-Ala-L-Ala-L-Pro-L-Phe-p-nitroanilide (AAPF). The protease cleaves the substrate and releases pNA. The release of the pNA causes an increase in the absorbance at 410 nm, the progress over time of which is a measure of the enzymatic activity (cf. Del Mar et al., 1979). Measurement takes place at a temperature of 25° C., at pH 8.6, and a wavelength of 410 nm. The measurement time is 5 min and the measurement interval 20 s to 60 s.

Compared with Bacillus licheniformis, the yield with Bacillus pumilus as production organism increased considerably (cf. table 2). The values given are the relative measured protease activities for Bacillus pumilus which are based on the protease activity for Bacillus licheniformis obtained in each case, which was defined as 100%.

TABLE 2

| Plasmid No. | Relative protease activity (%) |
|---|---|
| 1 | 114 |
| 2 | 134 |
| 3 | 150 |

Example 2

In this example, the fermentative production of a protease (target protein) in *Bacillus pumilus* was investigated with expression constructs which comprised different promoters. The expression plasmids 1 and 3 were used with promoters as per SEQ ID No. 1 and SEQ ID No. 2 as described in example 1. A further expression plasmid (control) used was an expression plasmid which differs from plasmids 1 and 3 by virtue of the fact that instead of a promoter from *Bacillus pumilus* a *Bacillus licheniformis* promoter was used which is disclosed in the international patent application WO 91/02792 ("promoter of the ATCC 53926 alkaline protease gene"; cf. examples 5, 6 and FIG. 27 WO 91/02792). The *Bacillus pumilus* strain used was as in example 1 *Bacillus pumilus* DSM 14395 in which the gene spoIV (yqfD) has been functionally deactivated by means of a deletion.

This strain was transformed with the specified expression plasmids. The resulting production strains were used in a standard fermentation method in a 2 liter laboratory fermenter and the resulting protease activities were determined via the release of the chromophore para-nitroaniline (pNA) from the substrate suc-L-Ala-L-Ala-L-Pro-L-Phe-p-nitroanilide (AAPF) as described in example 1. Compared with the control strain, the yield with plasmids 1 and 3 increased considerably (cf. table 3). The values stated are the relative measured protease activities for the strains comprising plasmids 1 and 3 which are based on the protease activity for the control strain, which was defined as 100%.

TABLE 3

| Plasmid No. | Relative protease activity (%) |
|---|---|
| Control | 100 |
| 1 | 133 |
| 3 | 131 |

Example 3

Two different expression plasmids, as given below, which in each case comprise a gene coding for an amylase (target protein) and a functional promoter, were transformed both into a *Bacillus licheniformis* strain and also into a *Bacillus pumilus* strain. The transformed strains were used for the fermentative amylase production. The *Bacillus licheniformis* strain used is disclosed in the international patent application WO 91/02792. The *Bacillus pumilus* strain used was *Bacillus pumilus* DSM 14395 in which the gene spoIV (yqfD) has been functionally deactivated by means of a deletion. The promoters used were nucleic acid sequences as per SEQ ID No. 3 and SEQ ID No. 4 (amylase promoter from *Bacillus amyloliquefaciens*, as disclosed in Palva, I., Pettersson, R. F., Kalkkinen, N., Lehtovaara, P., Sarvas, M., Soderlund, H., Takkinen, K. and Kaariainen, L. "Nucleotide sequence of the promoter and NH2-terminal signal peptide region of the alpha-amylase gene from *Bacillus amyloliquefaciens*"; Gene 15 (1), 43-51 (1981)). The promoter is arranged in the respective expression plasmids in each case 5' upstream of the nucleic acid sequence which codes for the amylase. The following plasmids were used (table 4):

TABLE 4

| Plasmid No. | Promoter | Amylase gene |
|---|---|---|
| 4 | SEQ ID No. 3 | Coding for the protein according to Seq ID No. 2 from EP1307547 A2 |
| 5 | SEQ ID No. 4 | Coding for the protein according to Seq ID No. 2 from EP1307547 A2 |
| 6 | SEQ ID No. 1 | Coding for the protein according to Seq ID No. 2 from EP1307547 A2 |
| 7 | SEQ ID No. 2 | Coding for the protein according to Seq ID No. 2 from EP1307547 A2 |

After the transformation of the expression plasmids into the respective microorganisms, the resulting production strains were used in a standard fermentation method in a 2 liter laboratory fermenter (48 h culture time) and the resulting amylase activities were determined. To determine the amylolytic activity in TAU, a modified p-nitrophenylmaltoheptaoside whose terminal glucose unit is blocked by a benzylidene group is used; this is cleaved by amylase to give free p-nitrophenyl oligosaccharide which, for its part, is converted to glucose and p-nitrophenol by means of the auxiliary enzymes glucoamylase and alpha-glucosidase. Consequently, the amount of released p-nitrophenol is proportional to the amylase activity. The measurement takes place for example with the Quick-Start® test kit from Abbott, Abott Park, Ill., USA. The absorption increase (405 nm) in the test batch is detected at 37° C. over 3 min against a blank value by means of a photometer. Calibration takes place via an enzyme standard of known activity (for example Maxamyl®/Purastar® 2900 from Genencor with 2900 TAU/g). Evaluation takes place by means of plotting the absorption difference dE (405 nm) per min against the enzyme concentration of the standard.

Table 5 gives the relative measured amylase activities for *Bacillus pumilus* which are based on the amylase activity for *Bacillus licheniformis* obtained with plasmid 4 (promoter according to SEQ ID No. 3), which was defined as 100%.

TABLE 5

| Plasmid No. | Relative amylase activity (%) in *B. licheniformis* | Relative amylase activity (%) in *B. pumilus* |
|---|---|---|
| 4 | 100% | 376% |
| 5 | not determined | 212% |

Surprisingly, it has been found that the promoter according to SEQ ID No. 3 in *B. pumilus* (which naturally does not produce any of its own amylase) is particularly suitable for achieving a very high yield of heterologously expressed amylase.

Example 4

In this example the fermentative production of an amylase (target protein) in *Bacillus pumilus* was investigated with expression constructs which comprised different promoters. The expression plasmids 4, 6 and 7 were used with promoters as per SEQ ID No. 3, 1 and SEQ ID No. 2 as described in example 3. The *Bacillus pumilus* strain used was as in example 1 *Bacillus pumilus* DSM 14395 in which the gene spoIV (yqfD) has been functionally deactivated by means of a deletion. This strain was transformed with the specified expression plasmids. The resulting production strains were used in a standard fermentation method in a 2 liter laboratory fermenter and the resulting amylase activities were determined as described in example 3.

Table 6 gives the relative measured amylase activities for the aforementioned *B. pumilus* strains comprising the plasmids 4, 6 and 7, which are based on the amylase activity for the *B. pumilus* strain comprising plasmid 4, which was defined as 100%.

Compared with plasmid 4, which is already particularly suitable for the heterologous amylase expression in *B. pumilus* (cf. table 5), with plasmid 7 a similarly high yield and with plasmid 6 an even more improved amylase yield was achieved (cf. table 6).

TABLE 6

| Plasmid No. | Relative amylase activity (%) |
|---|---|
| 4 | 100 |
| 6 | 112 |
| 7 | 101 |

The invention claimed is:

1. A method for producing a protein by means of a microorganism comprising
   (a) introducing an expression construct into a microorganism which comprises a promoter and a nucleic acid coding for the protein;
   (b) expressing the protein in the microorganism,
   wherein the microorganism belongs to the species *Bacillus pumilus*; and
   wherein the microorganism is sporulation-inhibited as a result of deleting the gene spoIV (yqfD) or parts thereof.

2. The method according to claim 1, wherein the promoter comprises a nucleic acid sequence which is selected from
   (a) nucleic acid sequence which is at least 95% identical to the nucleic acid sequence given in SEQ ID No. 1;
   (b) nucleic acid sequence which is at least 95% identical to the nucleic acid sequence given in SEQ ID No. 2;
   (c) nucleic acid sequence which is at least 95% identical to the nucleic acid sequence given in SEQ ID No. 3; or
   (d) nucleic acid sequence which is at least 95% identical to the nucleic acid sequence given in SEQ ID No. 4.

3. The method according to claim 1, wherein the protein is not naturally present in the microorganism.

4. The method according to claim 1, wherein the protein is an enzyme.

5. The method according to claim 1, wherein the microorganism is *Bacillus pumilus* DSM 14395.

6. The method according to claim 1, wherein the microorganism is genetically modified.

7. A microorganism obtainable by a method comprising
   (a) introducing an expression construct into a microorganism which comprises a promoter and a nucleic acid coding for the protein;
   (b) expressing the protein in the microorganism,
   wherein the microorganism belongs to the species *Bacillus pumilus*; and
   wherein the microorganism is sporulation-inhibited as a result of deleting the gene spoIV (yqfD) or parts thereof.

8. The microorganism according to claim 7, wherein
   (a) the promoter comprises a nucleic acid sequence which is selected from
   (i) nucleic acid sequence which is at least 95% identical to the nucleic acid sequence given in SEQ ID No. 1;
   (ii) nucleic acid sequence which is at least 95% identical to the nucleic acid sequence given in SEQ ID No. 2,
   (iii) nucleic acid sequence which is at least 95% identical to the nucleic acid sequence given in SEQ ID No. 3; or
   (iv) nucleic acid sequence which is at least 95% identical to the nucleic acid sequence given in SEQ ID No. 4;
   or
   (b) the protein is not naturally present in the microorganism, or
   (c) the protein is an enzyme
   or
   (d) the microorganism is *Bacillus pumilus* DSM 14395, or
   (e) the microorganism is genetically modified.

9. The method according to claim 4, wherein the enzyme is an acidic cellulase, alpha-amylase, alpha-acetodecarboxylase, aminopetidase, amylase, arabanase, beta-glucanase, beta-glucosidase, beta-mannosidase, carageenase, carbohydrase, catalase, cellobiose-oxidase, cellulase, chymosin, endo-1,3-beta-glucanase, endo-1,3(4)-beta-glucanase, endo-1,4-beta-xylanase, endopeptidase, esterase, exopeptidase, G4-amylase, glucoamylase, glucose oxidase, glucosidase, glycolipase, hemicellulase, laccase, lipase, lysophospholipase, maltogenic amylase, mannanase, neutral protease, nuclease, oxidase, oxidoreductase, pectate lyase, pectinase, pectin esterase, pentosanase, perhydrolase, phospholipase, phytase, polygalacturonase, protease, proteinase, pullulanase, rennet enzyme, rhamnogalacturonase, subtilisin, tannase, transferase, transglutaminase, xanthanase, xylanase, xyloglucanase or mixtures thereof.

10. The method according to claim 9, wherein the enzyme is an alpha-amylase, a protease, or a mixture thereof.

11. The method of claim 8, wherein the enzyme is an acidic cellulase, alpha-amylase, alpha-acetodecarboxylase, aminopetidase, amylase, arabanase, beta-glucanase, beta-glucosidase, beta-mannosidase, carageenase, carbohydrase, catalase, cellobiose-oxidase, cellulase, chymosin, endo-1,3-beta-glucanase, endo-1,3(4)-beta-glucanase, endo-1,4-beta-xylanase, endopeptidase, esterase, exopeptidase, G4-amylase, glucoamylase, glucose oxidase, glucosidase, glycolipase, hemicellulase, laccase, lipase, lysophospholipase, maltogenic amylase, mannanase, neutral protease, nuclease, oxidase, oxidoreductase, pectate lyase, pectinase, pectin esterase, pentosanase, perhydrolase, phospholipase, phytase, polygalacturonase, protease, proteinase, pullulanase, rennet enzyme, rhamnogalacturonase, subtilisin, tannase, transferase, transglutaminase, xanthanase, xylanase, xyloglucanase or mixtures thereof.

12. The method of claim 11, wherein the enzyme is an alpha-amylase, a protease, or a mixture thereof.

* * * * *

UNITED STATES PATENT AND TRADEMARK OFFICE
CERTIFICATE OF CORRECTION

| | | |
|---|---|---|
| PATENT NO. | : 9,725,704 B2 | Page 1 of 1 |
| APPLICATION NO. | : 14/374556 | |
| DATED | : August 8, 2017 | |
| INVENTOR(S) | : Tobias Kueppers et al. | |

It is certified that error appears in the above-identified patent and that said Letters Patent is hereby corrected as shown below:

In the Claims

At Column 24, Line 28, Claim 9 "carageenase," should be -- carrageenase, --.

At Column 24, Line 42, Claim 11 "The method" should be -- The microorganism --.

At Column 24, Line 45, Claim 11 "carageenase," should be -- carrageenase, --.

At Column 24, Line 58, Claim 12 "The method" should be -- The microorganism --.

Signed and Sealed this
Eighth Day of May, 2018

Andrei Iancu
*Director of the United States Patent and Trademark Office*

SEQUENCE LISTING

```
<160> NUMBER OF SEQ ID NOS: 4

<210> SEQ ID NO 1
<211> LENGTH: 555
<212> TYPE: DNA
<213> ORGANISM: Bacillus pumilus

<400> SEQUENCE: 1
cagcgtgtag acaaaccttc gcattcgttg tcaggtctgc gcgccggtgc tcacgaatgt      60
caaattcgct ccgcgccagt gctcggcctt cctagacttc aaaggttttc tatcacgctg     120
aaaagaagac aaagtgctaa aataaagatc attttagcac tttgtcaaca atctggaacc     180
tgttatataa acaggttctt ttaaatgaca aaaacaatga taaaataata tttttttata     240
tcgaaattcg aaatagctgc tagacgtttc tacctatttt aaggcttttc gggtatcgaa     300
tatttctccg ataatggatc ataagaaaaa tagcatactt ccttttaat agataatcgc      360 tgaaacagta gaataaacat attttaccac tatttccaag tgacttaatt ccccaatttt     420
cgctaggact ttcacaaaaa ttcaggtcta ctcttatttg cctacttccc ttaaactgaa     480
tatacagaat aatcaaacgt ctcattctta tagactacgg atgattattc tgaaataaga     540
aaaaagggat gtgga                                                      555

<210> SEQ ID NO 2
<211> LENGTH: 197
<212> TYPE: DNA
<213> ORGANISM: Bacillus pumilus

<400> SEQUENCE: 2
taacaagaga aaggccgcca attaggcggt ttttcctttt cattaagaaa ggtgagatcg      60
atagaataaa agttggaaag atacaaaaca cctaatttaa aaatgaaata ttttgtaaaa     120
aataagaata ttctctcatt tactccaata tgaaacaatc gtatgatttt tgatatagga     180
cataaaggag gaatatg                                                    197

<210> SEQ ID NO 3
<211> LENGTH: 225
<212> TYPE: DNA
<213> ORGANISM: Bacillus lichenformis

<400> SEQUENCE: 3
tcgggacctc tttccctgcc aggctgaagc ggtctattca tactttcgaa ctgaacattt      60
ttctaaaaca gttattaata accaaaaaat tttaaattgg tcctccaaaa aaataggcct     120
accatataat tcattttttt tctataataa attaacagaa taattggaat agattatatt     180
atccttctat ttaaattatt ctgaataaag aggaggagag tgatc                     225

<210> SEQ ID NO 4
<211> LENGTH: 217
<212> TYPE: DNA
```

```
<213> ORGANISM: Bacillus amyloliquefaciens

<400> SEQUENCE: 4
attgagcctt tgatgactga tgatttggct gaagaagtgg atcgattgtt tgagaaaaga      60
agaagaccat aaaaatacct tgtctgtcat cagacagggt atttttatg ctgtccagac     120 tgtccgctgt gtaaaaataa ggaataaagg ggggttgtta ttattttact gatatgtaaa    180
atataatttg tataagaaaa tgagagggag agtgatc                             217
```